United States Patent [19]

Nishiyama et al.

[11] 3,989,502
[45] Nov. 2, 1976

[54] METHOD FOR CONTROLLING GROWTH OF TOBACCO SUCKERS

[75] Inventors: Ryuzo Nishiyama, Takatsuki; Ryohei Takahashi; Nobuyuki Sakashita, both of Kusatsu, all of Japan

[73] Assignees: Sumitomo Chemical Company, Limited; Ishihara Sangyo Kaisha Ltd., both of Osaka, Japan

[22] Filed: Oct. 22, 1974

[21] Appl. No.: 517,000

[30] Foreign Application Priority Data
Oct. 27, 1973 Japan.............................. 48-121032

[52] U.S. Cl. ................................................. 71/78
[51] Int. Cl.² ........................................... A01N 9/36
[58] Field of Search ........................................ 71/78

[56] References Cited
UNITED STATES PATENTS

| | | | |
|---|---|---|---|
| 3,472,920 | 10/1969 | Schroder | 71/87 |
| 3,620,712 | 11/1971 | Conklin | 71/78 |
| 3,705,929 | 12/1972 | Schroder | 71/87 |
| 3,760,044 | 9/1973 | Schroder et al. | 71/87 |
| 3,901,679 | 8/1975 | Hofer et al. | 71/78 X |
| 3,923,493 | 12/1975 | Melnikov et al. | 71/87 |

*Primary Examiner*—Joseph P. Brust
*Attorney, Agent, or Firm*—Stevens, Davis, Miller & Mosher

[57] ABSTRACT

Tobacco suckers can very effectively be controlled by applying a composition comprising as the active ingredient at least one phosphorothionoamidate represented by the formula:

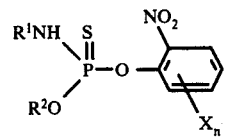

wherein $R^1$ and $R^2$ are independently alkyl groups having 1 to 4 carbon atoms; X is hydrogen, a halogen atom or an alkyl or alkoxy group having 1 to 4 carbon atoms; and $n$ is an integer of 1 to 3, around portions of tobacco at which suckers are to be developed or have slightly been developed.

7 Claims, No Drawings

METHOD FOR CONTROLLING GROWTH OF TOBACCO SUCKERS

This invention relates to a method for controlling tobacco suckers.

The utilization of chemical substances in agriculture has been greatly successful in fields such as insecticidal, microbicidal and herbicidal applications. On the other hand, regulating the growth of cultivated crop plants at will with chemical substances has been desired over a wide field in agricultural production, and many researchers have investigated it with a great interest. Nevertheless, there have been only a few examples of success. This means that the establishment of the plant growth regulating art is more difficult and requires more knowledges and experiences and an inventive sense. In the cultivation of tobacco, for example, the development of suckers results in a reduction in yield and quality of the crop. Therefore, the removal of suckers is indispensable, and doing this manually requires much labor and time. Therefore, many attempts have been made to control suckers with chemical substances, but few compounds have been found which effectively control suckers without damaging tobacco leaves, and new compounds therefor have long been desired.

The present inventors have done extensive research on plant-growth regulators to find that tobacco suckers can effectively be controlled by applying phosphorothionoamidate derivatives to tobacco under cultivation.

An object of this invention is to provide a method for controlling tobacco suckers.

Another object of this invention is to provide a method for effectively controlling tobacco suckers without damaging tobacco leaves.

Other objects and advantages of this invention will become apparent from the following description.

According to this invention, there is provided a method for controlling tobacco suckers, characterized by applying a composition comprising as the active ingredient at least one phosphorothionoamidate derivative represented by the formula:

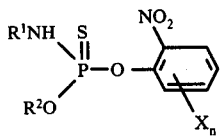

wherein $R^1$ and $R^2$ are independently alkyl groups having 1 to 4 carbon atoms; X is hydrogen, a halogen atom or an alkyl or alkoxy group having 1 to 4 carbon atoms; and n is an integer of 1 to 3, around portions of tobacco at which suckers are to be developed or have slightly been developed.

Some compounds included in the above formula and physical properties thereof are indicated below, but this invention is not restricted thereto:

(1) 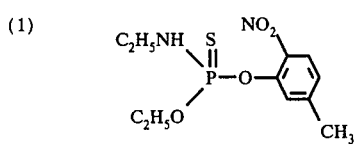  m.p.: 63 – 64° C (2) 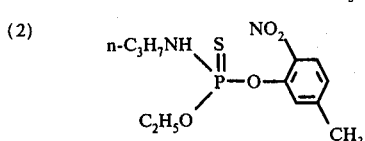  $n_D^{22.0}$: 1.5297

(3) 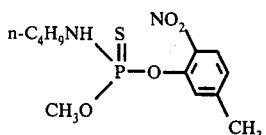  $n_D^{22.0}$: 1.5470

(4) 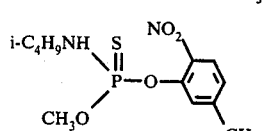  $n_D^{22.0}$: 1.5455

(5) 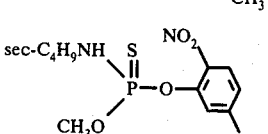  $n_D^{22.0}$: 1.5465

(6) 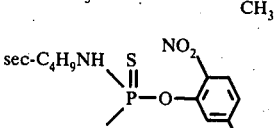  $n_D^{20.0}$: 1.5340

(7) 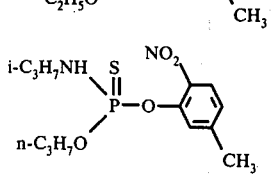  $n_D^{23.0}$: 1.5121

(8) 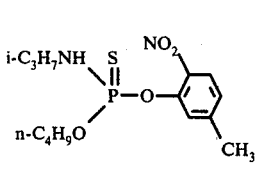  $n_D^{22.0}$: 1.5269

(9) 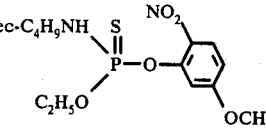  $n_D^{26.0}$: 1.5353

(10) 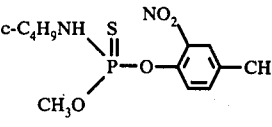  m.p.: 74 – 75° C

(11) 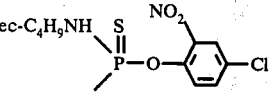  $n_D^{26.0}$: 1.5490

(12) 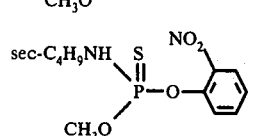  $n_D^{26.0}$: 1.5415

(13) 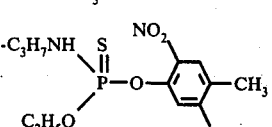  $n_D^{26.0}$: 1.5327

(14) 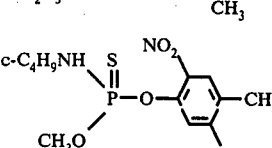  $n_D^{25.0}$: 1.5543

(15) 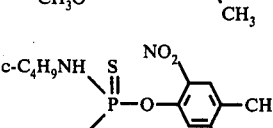  $n_D^{26.0}$: 1.5402

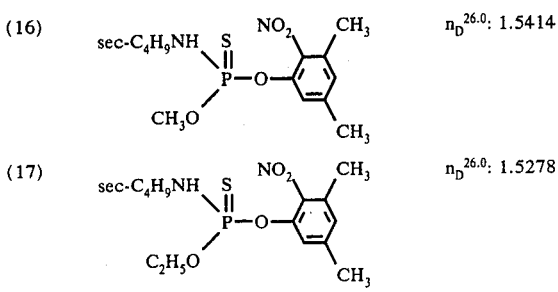

(16) $n_D^{26.0}$: 1.5414

(17) $n_D^{26.0}$: 1.5278

These compounds and analogous compounds are known as those having insecticidal, accaricidal, microbicidal or herbicidal activity in Czechoslovakian Pat. No. 127,221; U.S.S.R. Pat. No. 183,743; Belgian Pat. No. 745,633; Japenese Patent Publication No. 18,462/73, Dutch Pat. Nos. 6916095 and 6916096, DOS No. 2147873 and the like. However, some of the above patents are quite silent on the activity of the compounds to plants and some of them disclose only phytotoxicity against cultured plants and herbicidal effects of soil treatment with the compounds. None of the patents disclose or even suggest that tobacco suckers are effectively controlled by applying the phosphorothionoamidate derivatives directly to tobacco under cultivation without damaging the plant itself.

The composition used in this invention comprises the phosphorothionoamidate derivative represented by the above-mentioned general formula as the active ingredient and can be applied to tobacco under cultivation to control the development of suckers but not to damage the plant itself.

The composition comprising the compound represented by the above-mentioned general formula as the active ingredient is applied to tobacco under cultivation around portions at which suckers are to be developed or have slightly been developed, whereby the development of the suckers is very effectively controlled without imparting to the tobacco plant itself phytotoxicities such as inhibiting the elongation of plant height and damaging useful leaves. The composition of this invention has a sucker-controlling effect equal to or greater than that of commercially available maleic hydrazide type preparations, and gives useful tobacco leaves substantially no phytotoxicity. Therefore, the composition of this invention can safely be applied to various tobaccos, such as Bright yellow, Hickks, Burley, Xanthi, Havana, and the like.

The composition of this invention may be used in admixture with other compounds having a tobacco-sucker-controlling activity, such as aliphatic alcohols, for example, octanol, decanol or the like; fatty acids or their lower alkyl esters, for example, capric acid, nonylic acid, methyl caprate or the like; benzyl thiolcarbamate type compounds, for example, benzyl N,N-di-n-propylthiolcarbamate, 2-methylbenzyl N,N-di-n-propylthiolcarbamate, 4-chlorobenzyl N,N-di-n-propylthiolcarbamate, or the like; isopropyl-N-(3-chlorophenyl)-carbamate; and diethanolamine salts of maleic hydrazide, with the result that a higher, sucker-controlling effect is obtained than when each of the compounds of this invention is used alone.

The concentration of the active ingredient in the composition at the time of application and the amount of the composition applied to tobacco may vary depending upon the kind of tobacco, and the time and method of application of the composition, and cannot be defined indiscriminately. In general, however, the application concentration ranges from 100 to 10,000 ppm., preferably from 1,000 to 7,000 ppm., and the amount per tobacco plant ranges from 10 to 100 ml, preferably from 20 to 40 ml when the composition is applied at said concentration.

Although variable depending upon the kind of tobacco and culturing conditions, the application of the present composition is generally effected suitably at the topping stage, more particularly, between 2 weeks before the optimum period of topping and 2 weeks after the optimum period of topping, and most preferably within one week after topping. However, if said application is insufficient, the composition may be applied again thereafter.

An example of application of the present composition is the spraying of the composition around portions of crop at which suckers are to be developed or have slightly been developed, or the applying thereof so that the composition flows down along the stem of plant.

The composition of this invention may be of various formulations as in the case of conventional pesticides. For example, the above active ingredient compound may directly be dispersed in water, or may first be dissolved in an organic solvent, such as benzene, alcohols, acetone, xylene, methylnaphthalene, dioxane, cyclohexanone, and the like, or supported on a solid carrier such as talc, bentonite, clay, kaolin, diatomaceous earth, vermiculite, calcium hydroxide, and the like, and then dispersed in water. In this case, an agriculturally acceptable adjuvant, such as a dispersing agent, a penetrating agent or a spreader, may be added to the composition to obtain a more desirable result. Furthermore, the composition of this invention may be used in admixture with a conventional insecticide, microbicide or accaricide.

This invention is explained in further detail below referring to Examples, which are by way of illustration and not by way of limitation.

EXAMPLE 1

O-ethyl-O-(2-nitro-5-methylphenyl)-N-sec-butyl-phosphorothionoamidate [formula (6)] was dispersed in water to prepare an aqueous dispersion having a predetermined concentration, which was used as the present tobacco-sucker-controlling preparation in the following tests.

MH (the active ingredient: diethanolamine salt of maleic hydrazide) which is a commercially available tobacco-sucker-controlling preparation was diluted with water to prepare an aqueous dilution having a predetermined concentration, which was used as control in Test 2.

TEST 1

In a 1/500-are pot was placed soil, in which tobacco (variety: Bright yellow) was cultured in a greenhouse. When the plant height reached about 80 cm (i.e., just before blooming), terminal buds were removed, after which each test preparation was applied by means of a spray gun around axils of tobacco in a proportion of 20 ml per tobacco plant. The suckers were removed 50 days after the treatment, and the fresh weight thereof was measured. Simultaneously, phytotoxicity given to useful leaves was observed with the naked eye. The fresh weight per plant was determined and applied to the following equation to calculate the sucker-controlling percentage of each case, which is shown in Table 1:

$$\text{Sucker-controlling percentage (\%)} = \left\{1 - \frac{\text{Fresh weight of sucker per plant in treated pot}}{\text{Fresh weight of sucker per plant in untreated pot}}\right\} \times 100$$

Table 1

| Run No. | Test compound | Concentration (ppm) | Sucker-controlling percentage (%) | Phytotoxicity |
|---|---|---|---|---|
| 1 | O-ethyl-O-(2-nitro-5-methylphenyl)-N-sec-butylphosphorothionoamidate [formula (6)] | 1,000 | 70 | None |
| 2 | Same as above | 2,000 | 90 | None |
| 3 | Same as above | 4,000 | 100 | None |

TEST 2

A tobacco seedling (variety: Bright yellow) was transplated and cultured in a field, and when the plant height reached about 2 m (just before blooming) the suckers and terminal buds were removed, after which each test preparation was applied around axils of tobacco in a proportion of 30 ml per plant by means of a spray gun. In the same manner as in Test 1, the fresh weight of suckers was measured 30 days after the treatment and the sucker-controlling percentage ws calculated. Simultaneously, phototoxicity given to useful leaves was observed with the naked eye to obtain the results shown in Table 2.

Table 2

| Run No. | Test compound | Concentration (ppm) | Sucker-controlling percentage (%) | Phytotoxicity |
|---|---|---|---|---|
| 1 | O-ethyl-O-(2-nitro-5-methylphenyl)-N-sec-butylphosphorothionoamidate [formula (6)] | 4,000 | 100 | None |
| 2 | Same as above | 6,000 | 100 | None |
| 3 | MH | 5,000* | 89 | None |

Note:
*Concentration of MH is that of maleic hydrazide which is the active ingredient.

EXAMPLE 2

Soil was placed in a pot of 12 cm in diameter, in which a tobacco (variety: MC) was cultured in a greenhouse. When the plant height reached about 40 cm the terminal buds were removed, after which a test preparation prepared in the same manner as in Example 1 and having a concentration of 1,000 ppm. was applied in a proportion of 15 ml per plant around axils of tobacco by means of a spray gun. The suckers were removed 25 days after the treatment, and the fresh weight of the suckers was measured. Simultaneously, phytotoxicity given to useful leaves was observed with the naked eye to obtain the results shown in Table 3. The sucker-controlling percentage in each case shown in Table 3 was calculated according to the equation shown in Example 1.

Table 3

| Run No. | Test compound | Sucker-controlling percentage (%) | Phytotoxicity |
|---|---|---|---|
| 1 | O-ethyl-O-(2-nitro-5-methylphenyl)-N-ethyl-phosphorothionoamidate (1) | 100 | None |
| 2 | O-ethyl-O-(2-nitro-5-methylphenyl)-N-n-propyl-phosphorothionoamidate (2) | 100 | None |
| 3 | O-methyl-O-(2-nitro-5-methylphenyl)-N-n-butyl-phosphorothionoamidate (3) | 100 | None |
| 4 | O-methyl-O-(2-nitro-5-methylphenyl)-N-isobutyl-phosphorothionoamidate (4) | 100 | None |
| 5 | O-methyl-O-(2-nitro-5-methylphenyl)-N-sec-butyl-phosphorothionoamidate (5) | 100 | Small to middle. Young leaves were dwarfed. |
| 6 | O-n-propyl-O-(2-nitro-5-methylphenyl)-N-isopropyl-phosphorothionoamidate (7) | 100 | None |
| 7 | O-n-butyl-O-(2-nitro-5-methylphenyl)-N-isopropyl-phosphorothionoamidate (8) | 100 | None |
| 8 | O-ethyl-O-(2-nitro-5-methoxyphenyl)-N-sec-butyl-phosphorothionoamidate (9) | 100 | None |
| 9 | O-methyl-O-(2-nitro-4-methoxyphenyl)-N-sec-butyl-phosphorothionoamidate (10) | 100 | None |
| 10 | O-methyl-O-(2-nitro-4-chlorophenyl)-N-sec-butyl-phosphorothionoamidate (11) | 100 | None |
| 11 | O-methyl-O-(2-nitrophenyl)-N-sec-butylphosphorothionoamidate (12) | 100 | None |
| 12 | O-ethyl-O-(2-nitro-4,5-dimethylphenyl)-N-isopropyl-phosphorothionoamidate (13) | 100 | None |
| 13 | O-ethyl-O-(2-nitro-4,5-dimethylphenyl)-N-sec-butyl-phosphorothionoamidate (15) | 100 | None |
| 14 | O-ethyl-O-(2-nitro-3,5-dimethylphenyl)-N-sec-butyl-phosphorothionoamidate (17) | 100 | None |
| 15 | O-methyl-O-(2-nitro-4,5-dimethylphenyl)-N-sec-butyl-phosphorothionoamidate (14) | 100 | None |
| 16 | O-methyl-O-(2-nitro-3,5-dimethylphenyl)-N-sec-butyl-phosphorothionoamidate (16) | 100 | Small. Young leaves were dwarfed. |

EXAMPLE 3

| | | Parts by weight |
|---|---|---|
| (1) | O-ethyl-O-(2-nitro-5-methylphenyl)-N-sec-butylphosphorothionoamidate [formula (6)] | 40 |
| (2) | Xylene | 50 |
| (3) | Polyoxyethylene lauryl ether | 10 |

These components were uniformly mixed to prepare an emulsifiable concentrate.

EXAMPLE 4

| | | Parts by weight |
|---|---|---|
| (1) | O-ethyl-O-(2-nitro-4,5-dimethylphenyl)-N-sec-butyl-phosphorothionoamidate [formula (15)] | 40 |
| (2) | Xylene | 50 |
| (3) | Polyoxyethylene glycol | 10 |

These components were uniformly mixed to prepare an emulsifiable concentrate.

EXAMPLE 5

| | Parts by weight |
|---|---|
| (1) O-methyl-O-(2-nitro-5-methyl-phenyl)-N-sec-butylphosphoro-thionoamidate [formula (5)] | 40 |
| (2) Kaolin | 55 |
| (3) Sodium alkylbenzenesulfonate | 5 |

These components were uniformly mixed to prepare a wettable powder.

What is claimed is:

1. A method for controlling tobacco suckers characterized by applying around portions of the tobacco in which suckers are to be developed or have been slightly developed a composition comprising as the active ingredient 100 to 10,000 ppm of a compound selected from the group consisting of O-ethyl-O-(2-nitro-5-methylphenyl)-N-sec-butyl-phosphorothionoamidate, O-ethyl-O-(2-nitro-5-methylphenyl)-N-ethylphosphorothionoamidate, O-ethyl-O-(2-nitro-5-methylphenyl)-N-n-propylphosphorothionoamidate, O-methyl-O-(2-nitro-5-methylphenyl)-N-n-butylphosphorothionoamidate, O-methyl-O-(2-nitro-5-methylphenyl)-N-isobutylphosphorothionoamidate, O-methyl-O-(2-nitro-5-methylphenyl)-N-sec-butylphosphorothionoamidate, O-n-propyl-O-(2-nitro-5-methylphenyl)-N-isopropylphosphorothionoamidate, O-n-butyl-O-(2-nitro-5-methylphenyl)-N-isopropylphosphorothionoamidate, O-ethyl-O-(2-nitro-5-methoxyphenyl)-N-sec-butylphosphorothionoamidate, O-methyl-O-(2-nitro-4-methylphenyl)-N-sec-butylphosphorothionoamidate, O-methyl-O-(2-nitro-4-chlorophenyl)-N-sec-butylphosphorothionoamidate, O-methyl-O-(2-nitrophenyl)-N-sec-butylphosphorothionoamidate, O-ethyl-O-(2-nitro-4,5-dimethylphenyl)-N-isopropylphosphorothionoamidate, O-ethyl-O-(2-nitro-4,5-dimethylphenyl)-N-sec-butylphosphorothionoamidate, O-ethyl-O-(2-nitro-3,5-dimethylphenyl)-N-sec-butylphosphorothionoamidate, O-methyl-O-(2-nitro-4,5-dimethylphenyl)-N-sec-butylphosphorothionoamidate, and O-methyl-O-(2-nitro-3,5-dimethylphenyl)-N-sec-butylphosphorothionoamidate, wherein the composition is applied in a proportion of 10 to 100 ml per tobacco plant.

2. A method according to claim 1, wherein the composition is applied at the topping stage.

3. A method according to claim 1, wherein the compound is O-ethyl-O-(2-nitro-5-methylphenyl)-N-sec-butylphosphorothionoamidate.

4. A method according to claim 1, wherein the composition is in the form of a dispersion in water.

5. A method according to claim 4, wherein the composition further contains a dispersing agent, a penetrant or a spreader.

6. A method according to claim 1, wherein the composition is applied by spraying.

7. A method according to claim 1, wherein the composition is applied so that the composition flows down along the stem of the tobacco plant.

* * * * *